United States Patent [19]

Horn et al.

[11] Patent Number: 6,084,116
[45] Date of Patent: Jul. 4, 2000

[54] PROCESS FOR PREPARING ACETOXYSILANES

[75] Inventors: Michael Horn; Albert-Johannes Frings; Peter Jenkner; Jaroslaw Monkiewicz, all of Rheinfelden; Burkhard Standke, Loerrach; Bertram Trautvetter, Rheinfelden, all of Germany

[73] Assignee: Degussa Huels Aktiengesellschaft, Frankfurt, Germany

[21] Appl. No.: 09/374,843

[22] Filed: Aug. 16, 1999

[30] Foreign Application Priority Data

Aug. 14, 1998 [DE] Germany .............................. 198 37 010

[51] Int. Cl.[7] ...................................................... C07F 7/08
[52] U.S. Cl. ............................................................. 556/442
[58] Field of Search ............................................... 556/442

[56] References Cited

U.S. PATENT DOCUMENTS

| | | | |
|---|---|---|---|
| 4,332,956 | 6/1982 | Tolentino | 556/442 |
| 5,817,853 | 10/1998 | Friedrich et al. | 556/442 |
| 5,817,854 | 10/1998 | Horn et al. | 556/442 |

*Primary Examiner*—Paul F. Shaver
*Attorney, Agent, or Firm*—Oblon, Spivak, McClelland, Maier & Neustadt, P.C.

[57] ABSTRACT

Acetoxysilanes are prepared by a process comprising:

(i) reacting at least one chlorosilane with acetic acid in a medium containing acetyl chloride and a catalyst, and removing the hydrogen chloride which is formed during the reaction;

(ii) reacting the reaction mixture from step (i) with acetic anhydride; and (iii) separating and obtaining the product acetoxysilane.

24 Claims, No Drawings

PROCESS FOR PREPARING ACETOXYSILANES

BACKGROUND OF THE INVENTION

1. Field of the Invention

The present invention relates to a process for preparing acetoxysilanes by rearing chlorosilanes with acetic acid and acetic anhydride in the presence of a catalyst. More particularly, the present invention relates to the preparation of di-tert-butoxydiacetoxysilane.

2. Description of the Background

Acetoxysilanes have found wide application in the chemical industry. They are suitable, for example, as crosslinking silicon compounds in the production of polymer compositions which can be stored in the absence of water and are curable in the presence of moisture even at room temperature. Examples are compounds such as methyl-, ethyl- and propyltriacetoxysilane.

It is known that organoalkoxysilanes can be prepared by reacting the corresponding chlorosilanes with anhydrous sodium acetate, with acetic anhydride or with acetic acid. The yield of this reaction can also be increased if it is conducted in the presence of a tertiary base. Furthermore, tetreacetoxysilane can also be obtained from silicon tetrachloride and acetic acid in a low-boiling organic solvent, e.g. ether [W. Noll, Chemie und Technologie der Silicone, VCH Weinheim, pages 78 and 79 (1960); Inorganic Syntheses Vol. IV, pages 45–47 (1953)].

U.S. Pat. No. 2,566,347 describes how carbonoyloxysilanes can be prepared under controlled conditions from a halosilane and an organic carboxylic acid in liquid organic solvents such as pentane, ethyl bromide, isopropyl ether, benzene and carbon tetrachloride. Tetracetoxysilane can be converted, for example, into a dialkoxydiacetoxysilane by reaction with a corresponding amount of an alcohol.

FR 1 003 073 discloses the batchwise and simultaneous preparation of carbonoyloxysilanes and carboxylic acid chlorides by reacting organochlorosilanes with monocarboxylic anhydrides.

EP 0 845 469 teaches a process for preparing organocarbonoyloxysilanes by a catalyzed reaction of organochlorosilanes with a carboxylic acid and a carboxylic anhydride in two reaction steps. It is found that secondary reactions, for example, the thermal decomposition of the product formed or a reaction of HCl with acetic acid, can occur to an increased extent in the absence of a solvent, which leads to a significant decrease in yield.

One embodiment of said process is conducted using hexane as solvent.

In the first reaction step, acetic acid is added to an initially charged mixture of alkylchlorosilane and hexane at the boiling point, with hydrogen chloride being evolved.

In the second step, the resulting reaction mixture is added to excess acetic anhydride. Acetyl chloride is formed as a product of the reaction and it and hexane are removed by distillation. After removal of excess acetic anhydride, the crude acetoxysilane remains.

The acetyl chloride/hexane mixture obtained can be hydrolyzed with the equivalent amount of water to give an acetic acid/hexane mixture, which is subsequently separated by distillation and then returned to the synthesis.

As solvents or diluents, EP 0 845 469 also discloses pentane, benzene, toluene and trichloroethylene.

However, the following comments may be made on this intrinsically advantageous process:

In order to avoid introducing free water into the system, the acetyl chloride/hexane hydrolysis has to be conducted very precisely. This procedure is equivalent to a titration which is costly and often subject to errors on an industrial scale. This is because water in the system produces siloxanes on contact with silanes, thereby reducing the quality of the product and also the yield.

After the reaction with water, the resulting acetic acid/hexane mixture has to be separated by distillation. This distillation is likewise costly and requires, among other things because of the high melting point of acetic acid, a complicated condensation system which is generally susceptible to malfunction.

In the first reaction step and in the acetyl chloride/hexane work-up, hydrogen chloride is discharged from a hexane-containing solution. This discharge presents the problem that considerable amounts of hexane can be passed into the waste gas handling system, where it is, for example, carried by inert gases and thus discharged into the atmosphere. A need, therefore, continues to exist for improvements in the synthesis of acetoxysilanes in good yields and purity.

SUMMARY OF THE INVENTION

Accordingly, one object of the present invention is to provide a process for preparing acetoxysilanes which makes it possible to essentially avoid the abovementioned problems Briefly, this object and other objects of the present invention as hereinafter will become more readily apparent can be attained in a process for preparing acetoxysilanes, comprising:

(i) reacting at least one chlorosilane with acetic acid in a medium containing acetyl chloride and a catalyst, and removing the hydrogen chloride which is formed during the reaction, (ii) reacting the reaction mixture from step (i) with acetic anhydride, and (iii) separating and obtaining the product acetoxysilane.

DETAILED DESCRIPTION OF THE PREFERRED EMBODIMENTS

It has now been found that the abovementioned problems of acetoxysilane synthesis can be substantially, advantageously reduced if the process, as disclosed in EP 0 845 469, is modified by employing a reaction medium containing acetyl chloride, thereby providing a multifunctional reaction medium and a resulting simple and economic process.

In the present invention, the acetyl chloride employed as the reaction medium simultaneously and advantageously fulfills the following functions:

(1) Acetyl chloride, in the form of its hydrolysis products, is a very water-soluble solvent. The waste gas discharged from a reaction medium containing acetyl chloride then consists essentially of water-soluble constituents and can be absorbed in a simple and advantageous manner in a water-fed scrubber (function as solvent).

(2) Because of its low boiling point, acetyl chloride limits the reaction temperature, in particular in step 1, and thus prevents the thermal decomposition of the acetoxysilane which is formed in the reaction or its possible, still chlorine-containing precursors (function as temperature limiter).

(3) Acetyl chloride also serves to entrain hydrogen chloride in the esterification reaction. As a result, the hydrogen chloride concentration in the reaction rupture remains appropriately low, which mitigates against the secondary reaction of HCl and acetic acid to form acetyl chloride and water (function as entrainer).

(4) Acetyl chloride does not readily dissolve hydrogen chloride, particularly when hot. As a result, the HCl concentration in the reaction mixture can likewise be kept low (function as diluent).

In the second step of the reaction, only acetyl chloride is formed instead of an acetyl chloride/hexane mixture.

(5) Partial reaction of acetyl chloride with water prevents an excess of water in the medium, which excess amount of water would otherwise hydrolyze the desired product or its precursors (function as water trap).

(6) In reaction step 1 of the next batch which follows an initial batch reaction the chlorosilane can advantageously be introduced directly into the acetyl chloride/ acetic acid mixture present after the hydrolysis (function as source of starting material).

The further reaction of acetyl chloride with acetic acid to form acetic anhydride is generally extremely slow under the conditions which prevail then and can, therefore, be disregarded.

The present invention accordingly provides a process for preparing acetoxysilanes by reacting chlorosilanes with acetic acid and acetic anhydride in the presence of a catalyst in the first step of the reaction, the chlorosilane reacts with acetic acid, and the hydrogen chloride which is formed is removed. The reaction mixture which is obtained in this manner reacts in the second reaction step, in which acetyl chloride is used as reaction medium, with acetic anhydride and the resulting product mixture is worked-up.

In reaction step 1 of the process of the invention, at least one chlorosilane of the formula $R_nSCl_{(4-n)}$ (I), where R is a linear, branched or cyclic alkyl group having from 1–6 carbon atoms or a phenyl or benzyl group and n is 0, 1, 2 or 3 is preferably used as the starting material for the reaction.

If desired, two or more different chlorosilanes of formula (I) can also be used in reaction step 1; in this case, the chlorosilane components can be added as individual components in succession or in the form of a mixture.

If a plurality of chlorosilanes is added as individual components in the process of the invention, the order of addition of the chlorosilanes preferably follows the order of increasing reactivity of the respective chlorosilanes.

Particularly preferred chlorosilane starting materials include those of formula (I), but not exclusively, tetrachlorosilane, vinyl-, methyl-, ethyl-, propyl- or phenyltrichlorosilane, dimethyldichlorosilane and 2-chloroethylmethyldichlorosilane.

In the process of the invention, the reactions are generally carried out in the presence of a catalyst. Preferred catalysts include organic acid amides, particularly preferably N-N-dimethylformamide.

In reaction step 1, the catalyst content is appropriately set at an amount from 0.001–0.2% by weight, particularly 0.002–0.005% by weight, based on the amount of chlorosilane starting material.

Furthermore, when conducting the first reaction step of the process, a mixture of acetic acid and acetyl chloride is preferably charged initially to the reaction system and the chlorosilane component is added thereto.

The reaction in step 1 is preferably conducted at the boiling point of the particular reaction mixture and also desirably at a pressure of from 900–1100 mbar abs.

In addition, reaction step 1 of the present process is preferably conducted using acetic acid in the amount required to react with, on average, 50 mol. % of the bound chlorine in the chlorosilane. In general, the hydrogen chloride which is formed is removed via the gas phase. Here, acetyl chloride serves, in an appropriate and economical way, as an entrainer.

In reaction step 2 of the present process, acetic anhydride is preferably charged initially to the reaction medium and then the reaction mixture from reaction step 1 is added, as formed in the above-described reaction. At the same time the acetyl chloride, which has formed, is removed by distillation. If desired, excess acetic anhydride can also be subsequently removed by distillation.

Reaction steps 1 and 2 of the present process are usually conducted at temperatures in the range of 40–120° C. Preferably, reaction step 1 is conducted at a temperature of 50–65° C. and reaction step 2 is preferably conducted at a temperature of 50–100° C.

Furthermore, all reactions of the present process are appropriately conducted under an inert gas atmosphere, in particular, with the exclusion of atmospheric moisture.

In addition, the reaction of step 2 is preferably conducted at the boiling point of a particular reaction mixture which has been formulated.

The reaction of step 2 of the present process is preferably conducted at a pressure in the range from 1 bar abs. to 1 mbar abs., appropriately commencing at atmospheric pressure and lowering the pressure as the reaction proceeds. Furthermore, in reaction step 2, acetic anhydride is preferably used in at least the amount required to convert the bound chlorine in the acetoxychlorosilane in the reaction mixture from reaction step 1 into acetyl chloride. In particular, acetic anhydride is used in an excess of up to 300% by weight, particularly preferably from 0.1–100% by weight, very particularly preferably from 50–100% by weight, based on the amount of chlorosilane used.

The product mixture obtained in the reaction of step 2 is advantageously worked-up by distillation, and acetyl chloride and any excess acetic anhydride are removed from the top of the column, thereby leaving the desired product at the base of the column. The resulting product is generally obtained in quantitative yield, based on the chlorosilane used. As a rule, it contains about 2% of oligomeric siloxanes and less than 10 ppm by weight of hydrolyzable chloride. If necessary, it can be further purified by distillation in a manner known per se.

It is advantageous to add water to the acetyl chloride fraction obtained from reaction step 2 by distillation and convert it into a mixture of acetyl chloride and acetic acid; the amount of water is preferably selected such that acetic acid is produced in an amount which is in turn necessary to react with, on average, 50 mol. % of the bound chlorine in the chlorosilane in reaction step 1.

The resulting mixture of acetyl chloride and acetic acid is preferably reused in the reaction of step 1. Losses of acetyl chloride can advantageously be compensated by a slight variation in the amount of water added. In general, this step completes the cycle of the present process.

Thus, the process of the invention is preferably employed to prepare the following compounds:

tetreacetoxysilane, vinyltriacetoxysilane, ethyltriacetoxysilane, methyltriacetoxysilane, propyltriacetoxysilane, dimethyldiacetoxysilane, phenyltriacetoxysilane or mixtures thereof for example of methyl- and ethyltriacetoxysilane.

The process of the invention can, in general, be conducted as follows: A one equivalent (1 eq) amount of trichlorosilane is reacted with 1.5 eq of acetic acid in a first step and then with 1.5 eq plus excess acetic anhydride in a second step. In addition to the acetyl chloride used in the reaction medium, the additional 1.5 eq of acetyl chloride produced in the second step, together with 1.5 eq of water, provide the 1.5 eq of acetic acid needed for the next batch. As a rule, 1 eq of acetoxysilane is obtained in the manner described above and shown in the following equations:

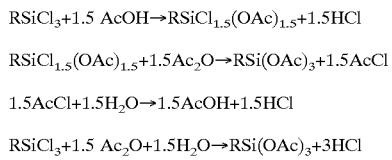

In practice, losses of acetyl chloride corresponding to its partial pressure can occur by way of the hydrogen chloride discharged from the reaction. This loss can be compensated by using somewhat less than 1.5 eq of water for the hydrolysis, thus also obtaining somewhat less than 1.5 eq of acetic acid, which, in the further course of the process, leads to an increased acetic anhydride consumption and thus to formation of more acetyl chloride. This processing aspect makes-up for the losses in an advantageous way.

The process of the invention can also be employed to prepare tetraacetoxysilane which is solid under the above-mentioned reaction conditions and which is sparingly soluble in the reaction medium. In this case, however, an apparatus suitable for solids handling should be employed in order to conduct the process steps, particularly in order to conduct necessary filtration operations.

The process of the invention can also be combined in a surprising, simple and economical and thus advantageous manner for the preparation of alkoxyacetoxysilanes. If, for example, it is desired to prepare di-tert-butoxydiacetoxysilane from tetraacetoxysilane, the tetreacetoxysilane obtained by the process of the invention can, immediately after the isolation of the solid, be reacted with the appropriate amount of alcohol, i.e., tert-butanol, in a manner known per se and the acetic acid liberated can be removed by distillation. In the process of the invention, the acetic acid obtained subsequent to reaction step 2 from the reaction of the tetreacetoxysilane with tert-butanol is appropriately used, at least in part, simply and economically in reaction step 1.

In the reaction of step 1, 75% of the Si-bonded chloride is preferably reacted with acetic acid so that, to advantage, essentially no other product apart from hydrogen chloride is formed:

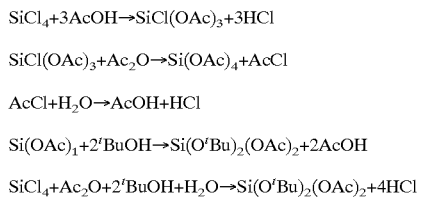

The operating procedure of the present invention in which acetyl chloride is used as reaction medium and, advantageously, functions simultaneously as solvent, diluent, entrainer, water trap, temperature limiter and source of starting material thus makes it possible to conduct the present process of preparing acetoxysilanes in a particularly economical and environmentally acceptable way.

Having generally described this invention, a further understanding can be obtained by reference to certain specific examples which are provided herein for purposes of illustration only and are not intended to be limiting unless otherwise specified.

EXAMPLES

Example 1

Preparation of Propyltriacetoxysilane

Apparatus A

A double-walled, oil-heated 1l multineck flask fitted with stirrer, a dropping funnel, water condenser, dry ice condenser (dry ice in isopropanol, set to about −40° C.). The apparatus is blanketed with nitrogen.

Apparatus B

A double-walled, oil-heated 1l multineck flask fitted with stirrer, a dropping funnel, a 50 cm packed column, column head with reflex divider and distillation receiver, water condenser, dry ice condenser (dry ice in isopropanol, set to about −40° C.). The apparatus is, on the one hand, to be blanketed with nitrogen; on the other hand, the apparatus is fitted with a vacuum unit which precedes a cold trap copied with dry ice.

First Batch of a Series

A 471 g (4.62 mol.) amount of acetic anhydride is placed in apparatus B and heated while stirring to 90° C. (heating bath: 120° C.). A 210 g (119 mol.) amount of propyltrichlorosilane is added thereto over a period of 4 hours. The acetyl chloride liberated in the reaction of these two compounds is removed by distillation at atmospheric pressure during the addition of the propyltrichlorosilane (offtake: reflux=2:1). When the reaction abates after the addition is complete, the heating temperature is reduced to about 100° C. and the pressure in the apparatus is reduced. Acetyl chloride continues to distill into the receiver (offtake: reflux=2:1). From about 250 mbar, the outlet of the distillation apparatus is closed and the reaction mixture is boiled further under reflux for about 2 hours. The temperature at the top first drops to just below the cooling water temperature. In this phase, acetyl chloride residues boil off through the water and low-temperature condensers and collect in the cold trap. Toward the end of the time indicated, the temperatures at the top of the column and in the reaction flask rise to a constant level. Distillation of the excess acetic anhydride is now commenced at about 50 mbar. At the end of this phase, the pressure in the apparatus is reduced to <3 mbar.

The following fractions are obtained:

Product: 290 g of propyltriacetoxysilane containing <1% of low boilers and <1% of high boilers Acetyl chloride: 241 ml 265 g from distillation receiver and cold trap, containing <2% of acetic anhydride Acetic anhydride: 145 g containing <1% of acetyl chloride The 265 g (3.38 mol.) amount of acetyl chloride are placed in apparatus A. The hearing temperature is set to 60° C. A 34.9 g (1.94 mol.) amount of water are added thereto over a period of 4 hours. The HCl liberated is conducted away. After the addition, heating is continued for another 30 minutes. A 225 g amount of acetyl chloride/acetic acid mixture (51% acetic acid) are obtained.

Second and Further Batches of a Series

1st Reaction Step

The acetyl chloride/acetic acid mixture obtained in apparatus A at the end of the previous batch, comprising about 16 g (1.93 mol.) of acetic acid, is treated with 3 drops of dimethylformamide and heated in apparatus A to the boiling point of acetyl chloride.

A 240 g (1.35 mol.) amount of propyltrichlorosilane is added thereto over a period of 4 hours. The HCl which is liberated is removed. After the addition, the mixture is boiled further for about 4 hours until the temperature in the reaction flask is constant. Analysis of the reaction mixture by gas chromatography demonstrates the presence of all possible reaction products of propyltrichlorosilane and acetic acid. Acetic acid is present in an amount of <0.5% and oligomers are present in an amount of <1%.

2nd Reaction Step

In the meantime, the acetic anhydride recovered from the previous batch (about 145 g) has been placed in apparatus B. A 212 g amount of fresh acetic anhydride is added thereto. The combined amounts (total of 3.5 mol. of acetic anhydride) are heated as described earlier in the description of the 1st batch. At a temperature in the reaction flask of 90° C., addition of the above-described reaction mixture from the 1st step is commenced. Addition conditions and distillation times correspond to those described above in the first batch.

The following fractions are obtained:

Product: 332 g of propyltriacetoxysilane containing <1% of low boilers and <2% of high boilers Acetyl chloride: 241 ml =265 g from distillation receiver and cold trap, containing <2% of acetic anhydride Acetic anhydride: 145 g containing <1% of acetyl chloride The acetyl chloride obtained is subsequently partially hydrolyzed as described above for the first batch of the series, thus completing one cycle.

Example 2

Preparation of a 2:1 Mixture of Ethyl- and Methyltriacetoxysilane

In apparatus A, 240 ml of acetyl chloride from a previous batch have been partially hydrolyzed using 34.2 g (1.90 mol.) of water.

1 st Reaction Step 3 drops of dimethylformamide are added to the acetyl chloride/acetic acid mixture obtained. A 139.7 g (0.854 mol.) amount of ethyltrichlorosilane is first added as described in Example 1 and the hydrogen chloride formed is removed. After the end of the addition, the mixture is heated further for about 1 hour.

In the meantime, the dropping funnel is recharged with 68.0 g (0.455 mol.) of methyltrichlorosilane which amount is metered into the reaction mixture subsequent to the further heating step. The reaction mixture is heated further until the temperature is constant and is then transferred to the dropping funnel of apparatus B.

2nd Reaction Step

In this process step, 345 g (3.38 mol.) of acetic anhydride are initially charged into the reactor and, as described in Example 1, the reaction mixture from step 1 is metered thereinto. All acetyl chloride and the excess of acetic anhydride are removed by distillation and the product is obtained as the bottoms of the distillation.

The following fractions are obtained:

Product: 298 g of acetoxysilane mixture (67% of ethyltriacetoxysilane,
33% of methyltriacetoxysilane) containing <1% of low boilers,
<1% of high boilers and <10 ppm of hydrolyzable chloride Acetyl chloride: 241 ml=265 g from distillation receiver and cold trap, containing <2% of acetic anhydride Acetic anhydride: 138 g containing <1% of acetyl chloride The disclosure of German priority application number 19837010.5 filed Aug. 14, 1998 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is desired to be secured by Letters Patent:

1. A process for preparing acetoxysilanes, comprising:
   (i) reacting at least one chlorosilane with acetic acid in a medium containing acetyl chloride and a catalyst, and removing the hydrogen chloride which is formed during the reaction;
   (ii) reacting the reaction mixture from step (i) with acetic anhydride; and
   (iii) separating and obtaining the product acetoxysilane.

2. The process as claimed in claim 1, wherein, in reaction step (i), the chlorosilane is added to a mixture of acetic acid and acetyl chloride.

3. The process as claimed in claim 1, wherein the reaction in step (i) is conducted at the boiling point of the reaction mixture present.

4. The process as claimed in claim 1, wherein the reaction in step (i) is conducted at a pressure of from 900–1100 mbar abs.

5. The process as claimed in claim 1, wherein, in reaction step (i), the amount of acetic acid is the amount required to react with, on average, 50 mol. % of the bound chlorine in the chlorosilane.

6. The process as claimed in claim 1, wherein, in reaction step (ii), acetic anhydride is initially charged, the reaction mixture from step (i) is added thereto, the acetyl chloride formed is removed by distillation and, optionally, excess acetic anhydride is subsequently removed by distillation.

7. The process as claimed in claim 1, wherein the reaction in step (2) is conducted at the boiling point of the reaction mixture.

8. The process as claimed in claim 1, wherein the reaction in step (ii) is conducted at a pressure in the range from 1 bar abs. to 1 mbar abs.

9. The process as claimed in claim 1, wherein, in step (ii), the amount of acetic anhydride is at least the amount required to convert the bound chlorine in the acetoxychlorosilane in the reaction mixture from step (i) into acetyl chloride.

10. The process as claimed in claim 9, wherein said amount of acetic anhydride is in an excess of up to 300% by weight, based on the amount of chlorosilane used.

11. The process as claimed in claim 1, wherein water is added in a controlled amount to the acetyl chloride separated in reaction step (ii) thereby converting the acetyl chloride into a mixture of acetyl chloride and acetic acid.

12. The process as claimed in claim 11, wherein the resulting mixture of acetyl chloride and acetic acid is returned to the reaction of step (i).

13. The process as claimed in claim 11, wherein the acetyl chloride separated in step (ii) is combined with the amount of water which is necessary to produce acetic acid in the amount required to react with, on average, 50 mol. % of the bound chlorine in the chlorosilane in step (i).

14. The process as claimed in claim 13, wherein losses of acetyl chloride are compensated by varying the amount of water.

15. The process as claimed in claim 1, wherein the catalyst is an organic acid amide.

16. The process as claimed in claim 15, wherein the catalyst is N,N-dimethylformamide.

17. The process as claimed in claim 1, wherein from 0.001–0.2% by weight of catalyst, based on the amount of chlorosilane, is employed in step (i).

18. The process as claimed in claim 1, wherein said chlorosilane of step (i) is at least one chlorosilane of formula 1:

 (I), where R is a linear, branched or cyclic alkyl group having from 1–6 carbon atoms, a vinyl, a phenyl group or a benzyl group and n is 0, 1,2 or 3, or dimethyidichlorosilane or 2-chloroethyimethyldichlorosilane.

19. The process as claimed in claim 18, wherein at least two different chlorosilanes of the formula (I) are present in step (i).

20. The process as claimed in claim 18, wherein, in step (i), chlorosilanes are added as individual components in succession or in the form of a mixture.

21. The process as claimed in claim 20, wherein the order of addition of a plurality of chlorosilanes follows the order of increasing reactivity of the chlorosilanes.

22. A process for preparing di-tert-butoxydiacetoxysilane, comprising:

(i) reacting at least one chlorosilane with acetic acid in the amount required to react with, on average, 75% of the bound chlorine in the chlorosilane in a medium containing acetyl chloride and a catalyst, and removing the hydrogen chloride which is formed during the reaction;

(ii) reacting the reaction mixture from step (i) with acetic anhydride thereby producing tetraacetoxysilane; and (iii) separating and obtaining the product di-tert-butoxydiacetoxysilane.

23. The process as claimed in claim 22, wherein the acetyl chloride separated in step (i) is combined with the amount of water which is necessary to produce acetic acid in the amount required to react with, on average, 25 mol. % of the bound chlorine in the chlorosilane in step (i).

24. The process as claimed in claim 22, wherein said product di-tert-butoxydiacetoxysilane is reacted with tert-butanol and at least part of the acetic acid obtained from the reaction is returned to step (i).

* * * * *